(12) United States Patent
Lyublinski

(10) Patent No.: US 6,358,397 B1
(45) Date of Patent: Mar. 19, 2002

(54) DOUBLY-PROTECTED REINFORCING MEMBERS IN CONCRETE

(75) Inventor: Efim Ya. Lyublinski, Beachwood, OH (US)

(73) Assignee: COR/SCI, Llc., Cleveland, OH (US)

( * ) Notice: Subject to any disclaimer, the term of this patent is extended or adjusted under 35 U.S.C. 154(b) by 0 days.

(21) Appl. No.: 09/663,958

(22) Filed: Sep. 19, 2000

(51) Int. Cl.[7] .............................................. C23F 13/00
(52) U.S. Cl. .................. 205/734; 205/725; 205/726; 205/727; 205/740; 205/733; 204/196.06; 204/196.17; 204/196.19; 204/196.23; 204/196.37; 204/196.24
(58) Field of Search ............... 204/196.24, 196.17, 204/196.19, 196.06, 196.05, 196.37, 196.21, 404, 196.23; 205/734, 725, 726, 727, 730, 732, 740, 776.5, 775.5, 733

(56) References Cited

U.S. PATENT DOCUMENTS

| | | | |
|---|---|---|---|
| 4,510,030 A | | 4/1985 | Miyashita et al. ............ 204/147 |
| 4,958,130 A | * | 9/1990 | Mochizuki et al. ......... 204/775.5 |
| 5,015,355 A | * | 5/1991 | Schiessi ....................... 204/404 |
| 5,100,738 A | | 3/1992 | Graf ............................ 428/613 |
| 5,141,607 A | * | 8/1992 | Swiat ........................... 204/196 |
| 5,792,337 A | * | 9/1998 | Padovani et al. ........... 205/775.5 |
| 6,165,346 A | * | 12/2000 | Whitmore .................... 204/734 |
| 6,224,743 B1 | * | 5/2001 | Satyanarayana ............. 205/74 |

* cited by examiner

*Primary Examiner*—Bruce F. Bell
(74) *Attorney, Agent, or Firm*—Renner, Otto, Boisselle & Sklar, LLP

(57) ABSTRACT

A concrete structure is reinforced with steel rebars coated with essentially pure aluminum in the range from about 0.25 mm to 2 mm thick upon which aluminum coating is an aluminum oxide layer in the range from 0.1 $\mu$m to 100 $\mu$m thick. This layer of aluminum oxide and/or hydrated aluminum oxide is referred to as a combined aluminum oxide layer, and it is in direct contact with the concrete. The Al-coated rebars may be protected in a galvanic circuit using magnesium or other metal baser than aluminum as a sacrificial anode, but more preferably the rebars are cathodically protected with an impressed cathodic current the current density of which is derived by sensing the corrosion potential at a sensing member of essentially pure aluminum embedded in the concrete, or in concrete outside a zone immediately surrounding the rebars, measuring the corrosion potential at the sensing member relative to a reference electrode until the value stabilizes at a measured stable potential; then providing an impressed current at a potential in the range from about 150 mV to less than 300 mV lower than the corrosion potential of the sensing member.

6 Claims, 7 Drawing Sheets

A -- Soluble Magnesium Anode
C -- Cathode     (Al-C) -- Aluminum Coating

DOUBLY-PROTECTED REINFORCING MEMBERS IN CONCRETE

BACKGROUND OF THE INVENTION

This application is directed to a system for the cathodic protection of reinforcing members referred to as "rebars" in conventionally reinforced concrete structures. Such rebars are produced from mild steel (also referred to as "black steel") which has less than 1% carbon and less than 2% of alloying elements, combined. More particularly the invention teaches a method of providing cathodic protection which is immediately commenced on newly embedded rebars in reinforced and/or prestressed concrete structures, that is, structures such as bridges, buildings including power stations, marine structures such as docks, and roadways which are yet to be built.

In applications where the cost of corrosion-protected rebars is justified, they have been coated with a synthetic resinous layer, typically an epoxide resin, which serves as a barrier against any liquid, thus denying formation of an electrochemical cell on the surface of the rebar. Such protection is referred to as "barrier protection" and is sometimes also obtained by painting rebars with a wide array of paints. Alternatively, rebars have been galvanically protected by being hot-dipped in zinc. Another alternative is to provide a rebar with both galvanic protection, and barrier protection. For example, some paints contain a high concentration of conductive metal such as zinc powder, or, metal salts such as zinc chromate.

Galvanized and aluminized steel products are commonplace as is the use of aluminum as an anodic metal. It is recognized that a thin aluminum film less than 0.2 mm thick, by itself, has limited protective function as a sacrificial anode because there is insufficient aluminum metal to be sacrificed over a long period of time in the range from 20 to 50 years. It is also recognized that a thicker coating of aluminum in the range greater than 0.2 mm thick up to about 1 mm thick, will provide effective protection as a sacrificial anode provided the aluminum itself is not destroyed by corrosive forces of its environment. Such corrosive forces exist in freshly poured concrete which has a pH above 9, up to about pH 13, which pH remains above 9 for several years while the concrete is curing, typically up to about 5 years, after which carbonation of the concrete, and acidification due to sulfur trioxide, acidic water and other factors, start to lower the pH of the concrete.

U.S. Pat. No. 5,100,738 to Graf teaches coating a rebar of a "steel alloy customary in reinforcing steels" (col 1, lines 58–59) immediately after rolling, with a layer of aluminum or aluminum alloy (together referred to as the "Al-layer"), then coating the once-coated rebar with a layer of a synthetic resin ("first layer"). The stated purpose of the Al-layer is that it "ensures reliable corrosion protection, in particular even when cracks appear in the first layer when in use, i.e. in particular upon bending of the reinforcing steel. In such cracks the second layer of aluminum or of aluminum alloy is exposed so that, until the concrete of a concrete structural part in which the reinforcing steel is imbedded sets, this layer then reacts with the free lime of the concrete of the cement with the assistance of oxygen to form a calcium aluminate, which ensures particularly solid and tight fusion with the reinforcing steel, so that no cracks, etc. into which moisture can penetrate occur or remain between the reinforcing steel and concrete. The first layer protects the second layer against external stresses of a chemical and/or mechanical nature." (see col 1, lines 21–36). This statement of how the Graf reinforcing member functions is reiterated at col 2, lines 27–48).

Since the function of the Al-layer is to provide the metal reactant for the free lime so as to form the calcium aluminate, there is no need for a thicker layer of Al metal than is required for the chemical reaction. Therefore Graf specifies that the Al-layer "is under 200 $\mu$m (micrometers)", preferably "in the order of magnitude of about 20 to 25 $\mu$m". Upon reaction the aluminum provides the calcium aluminate which "ensures particularly solid and tight fusion with the reinforcing steel" and concrete.

However, the desired reaction to form the calcium aluminate is not the only function of the Al coating because Graf states the Al-layer "contains zinc, while the percentage of aluminum is greater than 50% and, preferably, between about 55% and 70%." and, that "the percentage of zinc is smaller than 50% and, preferably, between about 28% and 43%." (see col 1, lines 44–49).

There is no teaching in Graf as to how the desired thin Al-layer is applied. However it is known that a layer of Al less than 200 $\mu$m thick conventionally applied on a rebar cannot be non-porous, and recognizing this, Graf also uses his Al-layer of Al-alloy to function as a sacrificial anode.

There is no indication as to whether the duty of the thin layer as a sacrificial anode is completed before the chemical reaction forming the calcium aluminate occurs because it is evident that if the calcium aluminate were to be formed first, there would be no protection from a sacrificial anode. Therefore one skilled in the art will appreciate that, depending upon the thickness of the metal layer, it will provide at least a measure of cathodic protection of the rebar, by virtue of the metal layer functioning as a sacrificial anode. Thus, with the Graf rebar protected with a coating of aluminum functioning both as a reactant and a sacrificial anode, it is clear that there is no reason to use such an anodically protected rebar as a cathode.

If there was no synthetic resinous layer overlying the very thin Al-layer on the rebars, then upon the rebars being embedded in freshly poured concrete, their entire surface would be transformed into a very thin calcium aluminate surface which presumably would not be expected to corrode. Since the calcium aluminate provides barrier protection, and there is no suggestion or reason to believe that the calcium aluminate layer provides any galvanic protection, it is evident that Graf did not believe such rebars could be used with an impressed current. Further, since Graf deliberately coated the Al-layer with an epoxy resin (stated only in claim 8) which is known to be electrically non-conductive, it would not be reasonable to use such a rebar with an impressed cathodic current of practical magnitude.

Still further, it is known that where an insulating layer of resin is provided on a metal surface which is then cathodically protected with an impressed current, and a break, crack or fissure exists in the resin which exposes the metal surface within the fissure, the exposed metal surface is protected, but the metal surface proximately surrounding the fissure becomes corroded causing the resin immediately above the corroding surface to be lifted from the metal surface. This phenomenon is more fully explained in a reference text titled "Handbuch des Kathodischen Korrosionsschutzes, 1980 (164–173)" which in relevant part states "Specific damage to steels results when a coating of non-ferrous metal (such as aluminum) is overlaid with a coating of resin and used in a cathodically protected system in which there is a break in the resin coating and the environment penetrates the break. Such damage is referred to as cathodic detachment. The generation of hydrogen by electrochemical reaction leads to separation of the resin coating and destruction of the metal with a high rate of corrosion."

Rather than forming a calcium aluminate and relying upon that for protection, this invention relies upon the discovery that a continuous and uninterrupted essentially non-porous thin aluminum oxide (Al-oxide) layer, or, hydrated Al-oxide (HAl-oxide) layer, less than 100 μm thick, typically in the range from 5 μm to 75 μm thick, on the surface of essentially pure aluminum coated on a rebar survives in freshly poured concrete having a pH above 9 and up to about 13, long enough to protect the Al metal until the concrete sets. Hereafter the term "combined Al-oxide layer" refers to a thin coating of aluminum oxide, or hydrated aluminum oxide, or both. This combined Al-oxide layer is corrosion resistant until destroyed.

Further, the combined Al-oxide layer fails to operate effectively to limit an impressed current sufficient to counter the potential at the cathode. The invention relies upon maintaining the combined Al-oxide coating for an arbitrarily long time despite the changing pH of the concrete environment of the rebar. The presence of the Al-oxide layer not only provides barrier protection but also unexpectedly lowers the current density ($mA/m^2$) required to provide effective cathodic protection relative to that required to protect virgin rebars which are not coated. The novel Al-coated rebars, without a coating of resin, are nevertheless doubly protected with two layers, (i) a first layer of essentially pure Al in contact with the rebar, and (ii) a second layer of alumina ($Al_2O_3$) overlying the layer of Al. Hereafter the term "Al-coated" refers to such a doubly protected rebar. Such Al-coated rebars have been found to be sufficiently conductive to be galvanically protected, preferably with magnesium.

Because an Al-oxide film forms essentially instantaneously on pure Al, and Al-coated rebars are embedded initially in an aqueous concrete environment, what is of interest are the Pourbaix diagrams for aluminum with an Al-oxide layer, and aluminum with a HAl-oxide layer. The Al-oxide layer shows immunity or passive behavior in the pH range from about 5 to 9; the HAl-oxide film shows immunity or passive behavior in the pH range from about 3 to 8.5 (see Corrosion Data, Aluminum and Aluminum Alloys, pg 16).

In a galvanic circuit, the metal to be protected becomes the cathode to which the anode is connected. For example, relative to the standard potential (in volts) at 25° C. of Hydrogen Reference Electrode (HRE)=0 V, of iron (Fe) is −0.440 V; that for zinc (Zn) is −0.763 V; that for Al is −1.66 V; and that for magnesium (Mg) is −2.37 V. The standard potential for Fe is given for the electrode reaction $Fe^{2+}+2e^-=Fe$; the potential for Al is given for the electrode reaction $Al^{3+}+3e^-=Al$; the potential for Zn is given for the electrode reaction $Zn^{2+}+2e^-=Zn$; and the potential for Mg is given for the electrode reaction $Mg^{2+}+2e^-=Mg$. In existing structures, the metals have corrosion potentials which will vary depending upon the environment. In a typical natural environment, the corrosion potential for Fe is in the range from −0.35 to −0.45 V, on average −0.4 V; for Zn is in the range from −0.70 to −0.80 V, on average −0.75 V; for Al is in the range from −0.50 to −0.60 V, on average −0.55 V; for Mg is in the range from −1.20 to −1.40 V, on average −1.30 V. Therefore, as is well known, Al does not behave as would be expected by virtue of its position in the EMF series.

Accordingly, aluminum or aluminum-rich alloy rods, or magnesium and magnesium-rich alloy rods, zinc and zinc-rich alloys were used as sacrificial anodes proximately disposed or embedded within the structure in galvanic connection with the steel rebars; or zinc-coated rebars were used; in either case, the required mass of the anode is the amount of metal which goes into solution over time, this amount of metal being the amount of electricity flowing through the galvanic circuit and the time over which the metal is consumed (Faraday's law). Since protection is sought over an extended time, and the rate of consumption of the anode is typically quite high once corrosion commences, the required mass of sacrificial anode for the long period, say 100 years, is high. Moreover, periodic replacement of anodes to provide continuous protection is inconvenient at best and often impractical. Therefore use of such sacrificial anodes has been largely discontinued in favor of using an external power supply to provide an impressed cathodic current to the corrodible metal. By controlling the impressed current the service life of the structure is not limited by corrosion of its steel reinforcement.

To avoid confusion, it should be noted that in galvanic cells, the cathode is the positive pole and the anode is the negative pole. The electrode at which chemical reduction occurs (or + electricity enters the electrode from the electrolyte) is called the cathode (e.g. $H^+ \rightarrow 1/2H_2-e^-$); and the electrode at which chemical oxidation occurs (or + electricity leaves the electrode and enters the electrolyte) is called the anode (e.g. $Zn \rightarrow Zn^{2+}+2e^-$). However, when current is impressed on a cell from a generator or an external battery, reduction occurs at the electrode connected to the negative pole of the external current source, and this electrode is therefore the cathode. Thus the cathode is the electrode at which current enters from the electrolyte, and the anode is the electrode at which current leaves to return to the electrolyte. Cations migrate towards the cathode when electricity flows through the cell and are positively charged; anions are negatively charged.

In cathodic protection, an impressed current is caused to flow through the anode into the electrolyte and then to the rebars in the structure. Such protection with the uncoated steel rebars as the cathode, as conventionally practiced, is expensive, requiring a much higher current density to obtain a satisfactorily low level of corrosion than that required to obtain the same corrosion protection with rebars coated with Al.

The real benefit of electrochemical protection is that one can obtain equivalent protection at much lower current density. This protection occurs when the electrochemical nature of the cladding comes into play. Further corrosion spreads laterally confining itself to the aluminum oxide and/or hydrated oxide cladding rather than penetrating into the steel core of the cathode. The rate of attack is affected by the relative size of the anode and the pH of the concrete environment; a small anode area in contact with a large cathode area will result in a rapid and severe attack. Because the degree of ionization of the cladding is so low, the rate of attack is low.

Despite numerous teachings as to how rebars may be protected against corrosion in concrete, current construction routinely uses virgin rebars which have been cut to length in a rolling mill and which have been oxidized in the atmosphere in which they were stored. Since the oxidized (ferrous and ferric oxides) coating on a rebar provides it with a substantial level of protection against the alkaline environment in freshly poured and cured concrete, there has been little incentive to protect rebars any further.

It is well known that aluminum and aluminum alloys may be cathodically protected with a sacrificial anode of magnesium or alloy lower in the electromotive series (that is, having a lower or more negative potential) than aluminum, but it is far more practical to provide protection with an impressed cathodic current. In an impressed current circuit, the article to be protected is the cathode, and the anode may be consumable but preferably is graphite or other non-consumed metal or alloy. The cathode and anode in a concrete environment provides salts dissolved in water as the electrolyte medium.

The concrete environment which is continually changing differentiates it from those for which numerous other cathodic protection systems are provided. Such other systems are provided for the hulls of boats and other large aluminum articles. Such articles differ greatly from rebars in that they have all relatively thick cross-sections of aluminum or aluminum alloys, typically at least 3 mm thick, and they are not in a concrete environment. Such thickness provides a large measure of latitude with respect to control of the impressed current because the pH of the immediate surroundings of the cathode and anode, for example sea water, changes within a relatively narrow range of from about pH 8 to 10.

U.S. Pat. No. 4,510,030 to Miyashita et al recognized the problem of corrosion of aluminum "having an anode oxide coating or a film of paint applied to the surface thereof or bare aluminum materials, immersed in water, against pitting or grain boundary corrosion by the application of the aforementioned sacrificial anode or cathodic protection method." (see col 2 lines 1–5). They teach that "aluminum material" will remain stable in water for a long time without undergoing substantial corrosion if the natural potential of the aluminum "is maintained in the narrow range from about 03 V to about 0.4 V below the pitting potential up to the pitting potential, . . . " (see col 2, lines 17–19). However, they teach that "when the voltage of the external power source is controlled so as to maintain the cathode potential at the portion in the vicinity of the opposite electrode of the aluminum material in a proper range, the potential at the portion remote from the opposite electrode is insufficiently repressed. On the other hand, when it is contemplated to repress sufficiently the potential at the portion remote from the opposite electrode of the aluminum material, the potential at the portion in the vicinity of the opposite electrode is excessively repressed. Such excessive repression of the potential tends to cause dissolution, i.e. alkali corrosion, of the aluminum material. As described above, when the conventional sacrificial anode method or cathodic protection method with use of the external power source is relied on, it is difficult to effect control of the cathode potential of the entire volume of the aluminum material so that the potential may remain in the stable range." (see col 2, line 61 to col 3, line 10).

Though Miyashita et al do not refer to the pH range which they wish to maintain, or to the range of current density (mA/m$^2$) required, it is clear that their system is directed to a sea water environment where the pH is about 9, and there is no suggestion that they can cope with a pH which is typically initially about pH 13. It is equally clear that they maintain a cathode potential in the range from −700 mV to about −1300 mV relative to a calomel electrode (see FIG. 2 of the '030 patent). Within this range a stable potential is maintained in the range from −700 mV to about −1000 mV such that the Al is stable. The circuits shown in FIGS. 1a and 1b (of '030) are short circuited when the potential reaches −700 mV which returns the potential to about −1300 mV. Because they can measure the potential at the protected aluminum surface itself they measure potential as it gradually changes until it approaches the corrosion potential of −700 mV when the current is switched on for a short time. They can never measure the changing potential as corrosion potential changes due to changing environmental conditions while the impressed current is on, and therefore cannot adjust the current as required. They can only short circuit. This deficiency is addressed in the present invention by using a corrosion potential sensing member connected in a circuit separate from the circuit which provides the impressed current for the rebars to be protected. In an environment of freshly poured concrete, the pH is initially in the range from about 12–14; upon commencing to cure the pH remains above pH 9 for about 50 years, after which the pH gradually decreases due to acidification of the concrete, into the range from about pH 5 to pH 9. In concrete with such high alkalinity any additional alkalinity due to a relatively low impressed current proves to be surprisingly insubstantial.

SUMMARY OF THE INVENTION

It is a general object of this invention to minimize, if not negate the damage caused by corrosion products of mild steel rebars, which products occupy a larger volume than the metal consumed; not only are the rebars weakened but also the concrete, which cracks and spalls.

It has been discovered that steel rebars coated with an essentially non-porous thin layer of essentially pure aluminum in the range greater than 250 μm but less than about 2 mm thick, preferably in the range from about 250 μm to 1 mm thick, non-removably integrated onto the surface of the rebars, and allowed to form a layer of substantially non-conductive aluminum oxide and/or hydrated aluminum oxide on the surface, function effectively as a cathode. Such rebars with a combined Al-oxide layer may be used with (a) an impressed current and an insoluble anode, or (b) a sacrificial soluble anode; in each case the service life of the protected structure is increased for an arbitrary and indefinitely long period. It is critical that the aluminum coating be of essentially pure aluminum which contains less than 2% of other metals and silicon combined, and that the pH in a zone immediately surrounding the rebar and its Al-oxide layer be maintained in a range in which the rate of corrosion is minimal, typically from about pH 9 to pH 6 though the initial pH of freshly poured concrete is about 13 and will typically decrease to pH 9 or lower after the concrete is exposed to an acidic environment over a period greater than 50 years. By "immediately surrounding" is meant a zone within a radius of 10 mm from the surface of an Al-coated rebar. By "minimal" is meant less than 20 μm/yr and preferably less than 10 μm/yr.

It is therefore a general object of this invention to provide a method for protecting steel components including reinforcing members such as rebars in re-inforced and pre-stressed concrete structures, by coating the rebars with the aforesaid thin essentially pure aluminum coating and allowing them to develop an Al-oxide coating in the range from about 0.1 μm to 100 μm thick before pouring the concrete around them so that the oxide surface is in direct contact with the concrete and is free from an additional layer of synthetic resinous material; and, electrically connecting the essentially non-conductive oxide as cathode in a circuit in which either an insoluble or soluble anode may be used to provide an impressed cathodic current, either anode being used on the surface of the structure, or, in close proximity with the structure, or, within it. Irrespective of the choice of effective positioning of the anodes, the anodes are an essential component of the protected structure and deemed to be essentially integral therewith.

It has unexpectedly been found that the cathodic Al-coating used herein is from 5 to 10 times thinner than a prior art coating which would have been used galvanically to afford the same protection against corrosion of steel rebars in concrete; moreover, using the aforesaid Al-coating reduces the amount of current required for the same degree of cathodic protection afforded by conventional cathodic protection of uncoated rebars, by a factor in the range from about 10 to 20, typically requiring a current density in the range from about 20 to 40 mA/m$^2$; the Al-oxide coating affords sufficient conductivity at a pH in the range from about 6 to 9 to have a surprisingly great effect on the cost of operation for protection allowing corrosion of 10 $\mu$m/yr compared to the cost of protection of coated rebars with a sacrificial coating of zinc, offering the same protection. As used hereafter, the term "Al-coating" refers to the coating of essentially pure aluminum which in turn is coated with a "combined Al-oxide layer".

More particularly, it has been discovered that the Al-coating is surprisingly resistant to alkali corrosion, provided an essentially continuous impressed current is maintained which is in the range from about 150 mV but less than 300 mV, most preferably 200 mV, lower than the corrosion potential of a corrosion potential sensing member of essentially pure Al embedded in concrete in a zone in which the pH is above 9 and up to about pH 13, such member being of the same metal as the coating on the rebars, namely an Al member of arbitrary shape, preferably a plate or rod; the potential of the impressed current required to provide desired protection of the Al-coated rebars in concrete is in the range from about –600 mV (–0.6 V) to about –1300 m (–1.3) relative to a HRE. In the curing or cured reinforced concrete structure, the impressed current represses the cathodic potential of the is rebars to within a predetermined range correlatable with a corrosion potential measured as the corrosion potential sensing member; further, the impressed current maintains a pH in a range from about 6 to about pH 9 in a zone within a radius of about 10 mm from the surface of an Al-coated rebar.

BRIEF DESCRIPTION OF THE DRAWING

The foregoing and additional objects and advantages of the invention will best be understood by reference to the following detailed description, accompanied with schematic illustrations of preferred embodiments of the invention, in which illustrations like reference numerals refer to like elements, and in which.

DETAILED DESCRIPTION OF PREFERRED EMBODIMENTS

Rebars coated with the aforesaid Al-coating and freshly embedded in concrete are immediately exposed to a pH of about 13 and are subject to alkali corrosion. Such rebars may be galvanically protected by being connected to a metal baser than Al, that is, having a lower standard potential than Al, as schematically illustrated in FIG. 2.

Figure 2:
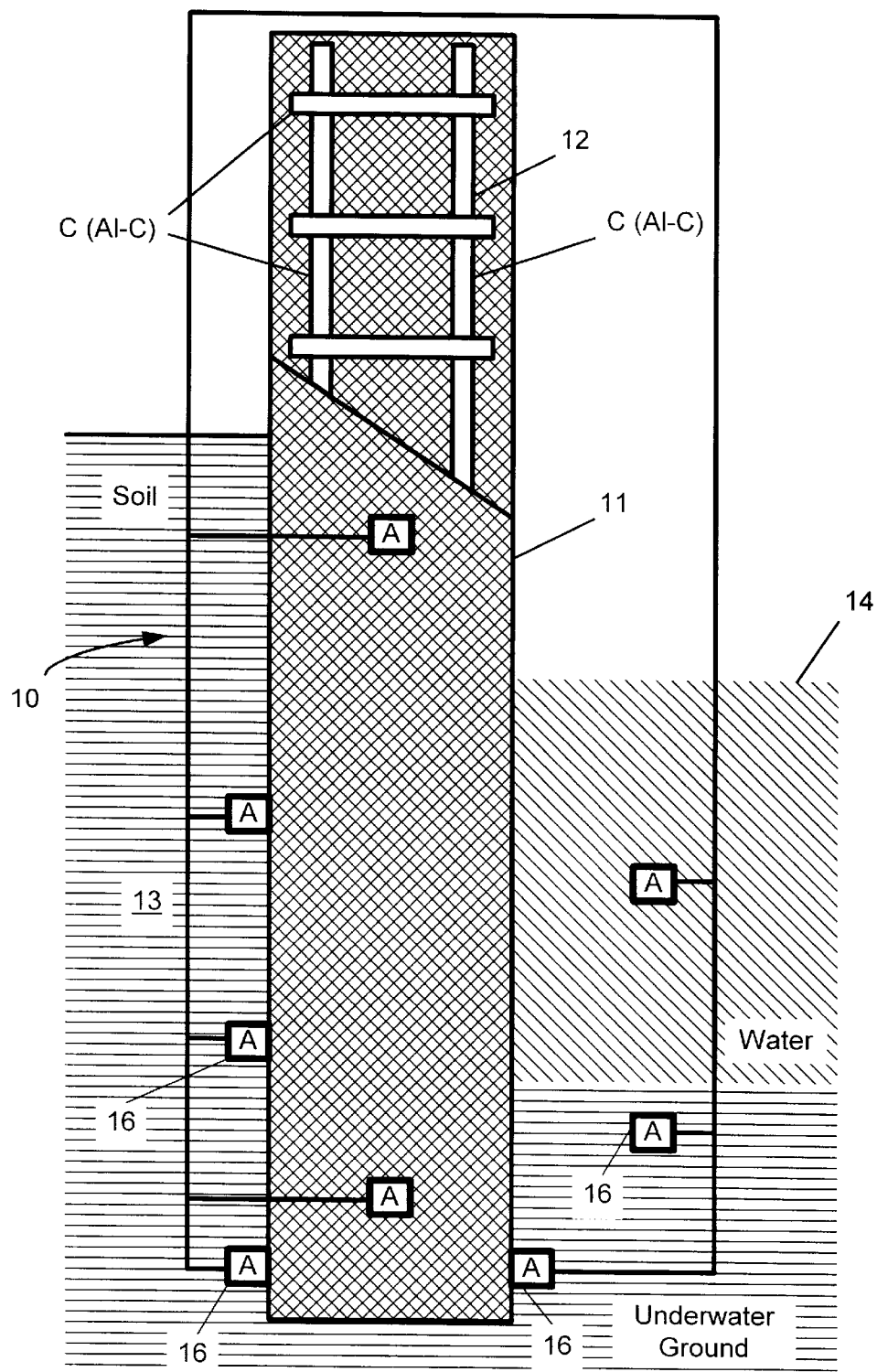
FIG. 2 is a side elevation view schematically illustrating a reinforced concrete structure in which its Al-coated steel rebars are cathodically protected by plural soluble magnesium anode proximately disposed relative to the rebars, externally and optionally, internally, all anodes being galvanically connected with the cathode.
Figure 3:
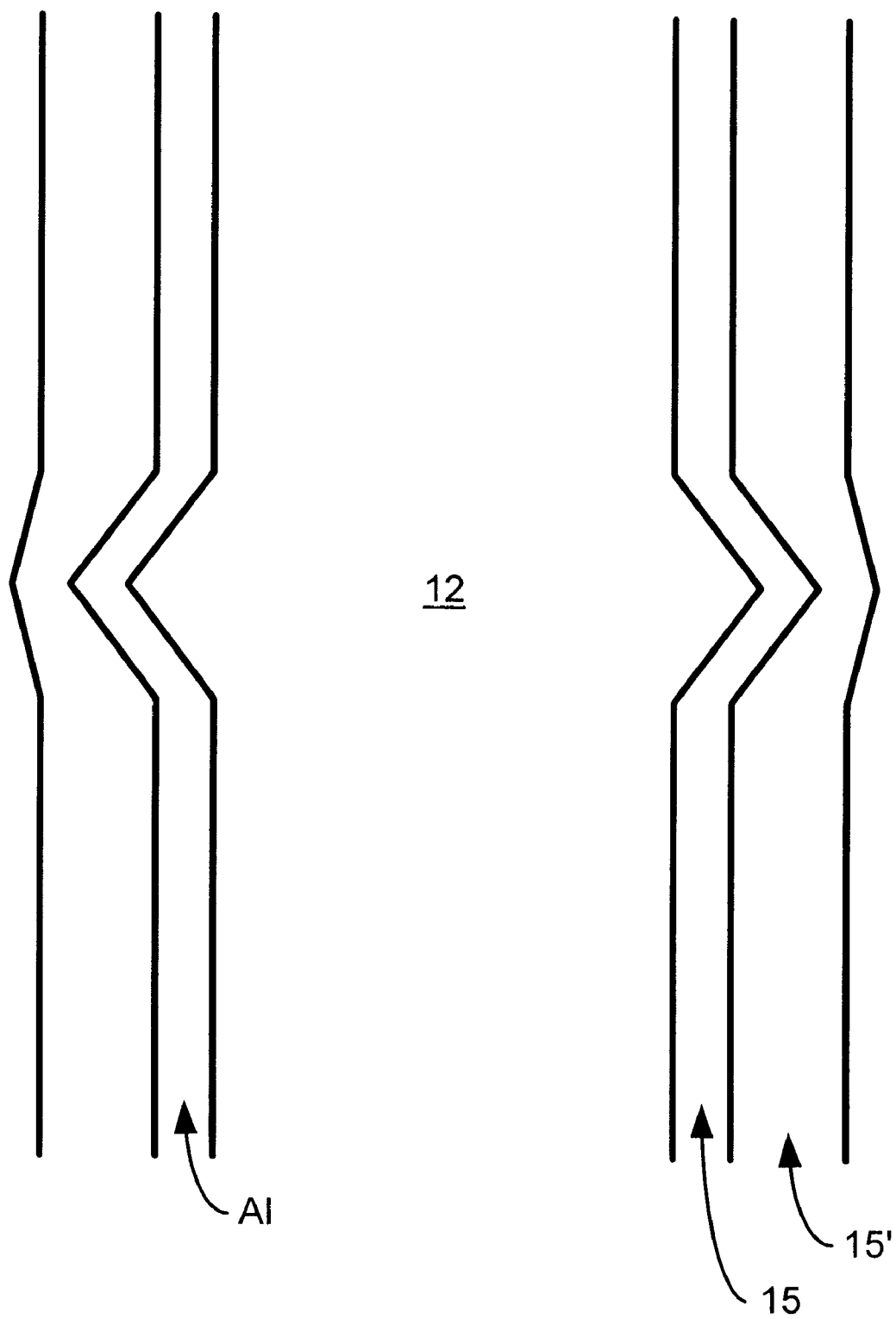
FIG. 3 is a detail showing a portion of a Al-coated rebar which has on its surface a very thin layer of aluminum oxide and/or hydrate aluminum oxide, referred to herein as a "combined Al-oxide layer".

Referring to FIGS. 2 and 3 there is illustrated a cathodically protected structure, indicated generally by reference numeral 10, exposed to the atmosphere. The structure includes a reinforced concrete column 11 within which is embedded a grid 12 of rebars appropriately secured together with wire "ties" of aluminum-coated steel wire (not shown). The concrete of column 11 is sufficiently porous to allow penetration by moisture and transport of electrons, and so is the soil 13 in which the column is anchored. A portion of the column is shown immersed in water 14. Preferably, all rebars are incorporated as the cathode in the system.

Before being embedded in the concrete, the rebars are coated with a layer 15 of essentially pure Al having a thickness in the range specified above, most preferably about 0.25 mm thick, as schematically illustrated in the detail of a portion of coated re-bar shown in FIG. 3. The manner in which the aluminum coating is applied is not narrowly critical provided that the aluminum coating adheres so strongly as to become an integral part of the rebar structure, and the coating is essentially non-porous. By "essentially non-porous" is meant that visual examination of the coated surface under a microscope indicates that the Al-oxide coating formed on the aluminum covers at least 95% of the surface of the rebar.

The rebars may be hot-dipped conventionally by pickling and cleaning to remove scale, rust and surface contaminants, and continuously passing through a furnace containing an oxidizing atmosphere maintained at a temperature of about 1093° C. (2000° F.) to burn off any remaining contaminants and form a thin oxide coating. The oxide-coated rebars are passed continuously through a furnace containing a reducing atmosphere (80% nitrogen/20% hydrogen) to reduce the oxide coating to a metallic surface free of non-metallic impurities and provide a surface to which the aluminum hot-dip coating will strongly adhere. The rebars are then dipped in molten aluminum in an inert atmosphere, and cooled in a controlled oxidation atmosphere without further heating to avoid forming a diffusion alloy coating, and without forming an intermediate layer comprising intermetallic compounds such as are formed as the reaction products between sheet steel and aluminum used to coat it, as for example in the manufacture of automobile exhaust systems and home appliances.

Alternatively, the re-bars may be spray coated using an electric arc in an inert atmosphere. Irrespective of how the Al coating is applied, it acquires a thin coating of Al-oxide 15' (shown greatly exaggerated and not to scale) which is always present; when embedded in freshly poured concrete a coating of hydrated aluminum oxide (HAl-oxide) is also formed, being integral with and a part of the Al-oxide layer 15'. Therefore the HAl-oxide layer is not separately identified. The thickness of the combined Al-oxide layer depends on the particular concrete environment, its temperature and the time the rebars are held in that environment. The thickness of the combined Al-oxide coating 15' is typically in the range from 0.5 $\mu$m to about 5 $\mu$m.

The column 11 is surrounded by plural anodes 16 of metal which forms a salt soluble in an aqueous environment, the metal preferably being magnesium or a magnesium-rich alloy; and, optionally, in a new structure, additional sacrificial anodes may be interspersed within the structure. Preferably the anodic area is provided is in the range from about 0.1 m$^2$ (square meter) to about 1 m$^2$ per 50 m$^2$ of bare cathode. The anodes 16 are vertically spaced apart from one another along the entire length of the column, the spacing from the column being sufficiently close, and a sufficient number of anodes 16 being used to provide the appropriate current density when the anodes are each electrically connected to the grid of rebars 12. Preferably some of the anodes are attached to the surface of the column, others are proximately spaced apart from the surface, some being in the water. All wires in the electrical circuit are appropriately insulated.

As Miyashita et al taught, "When the sacrificial anode is made of a metal possessing sufficiently baser natural potential than the aluminum so as to permit control of potential even in the portion of the aluminum material remotely separated from the sacrificial anode, the portion of the aluminum material close to the sacrificial anode is subjected to excessive potential which tends to induce the phenomenon of alkali corrosion due to so-called excessive anticorrosion." (see col 2, lines 50–58); and ". . . excessive repression of the potential tends to cause dissolution, i.e. alkali corrosion, of the aluminum material." (see col 3, lines 3–4). This difficulty is preferably overcome by using an inert anode and greatly decreased by using an impressed current in the range from 900 mV (0.9 V) to 1500 mV (1.5 V), as described in detail below, irrespective of the anode used, provided of course it is baser than Al.

With respect to using an impressed cathodic current to an aluminum cathode, Miyashita et al stated ". . . application of an anodic oxide coating on the surface of such aluminum materials and/or application of a film of paint to such surface have been accepted in actual practice and do prevent such corrosion at least to some extent." (see col 1, lines 34–38); and that "mere application of the conventional sacrifice anode method to such aluminum materials failed to afford the same satisfactory protection against corrosion as had been obtained for steel materials. The reason for this failure is that unlike steel, aluminum is a so-called amphoteric metal which dissolves in both acids and alkalis." (col 2, lines 6–12). Rather than Al being an amphoteric metal, the more likely reason is believed to be that Miyashita et al were dealing with a sea water environment, not concrete. They therefore missed realizing that a combined Al-oxide layer could provide excellent corrosion protection if used in conjunction with an essentially continuous impressed cathodic current.

Because of the much higher pH of freshly poured and newly curing concrete, a relatively small impressed anticorrosion cathodic current flowing to the Al-coated rebars from the negative terminal of an external power source at a potential $E_p$, keeps the potential of the rebars below the corrosion potential of the Al plate or rod embedded in the concrete (see FIG. 5). The high pH of concrete around the rebars negates any danger of the potential of the rebars rising above the corrosion potential $E_c$ of the Al plate or rod, and by, analogy, of the rebars. The potential $E_c$ is continuously monitored and the impressed current is provided such that $E_p = E_c + 200$ mV. The potential of the Al-coated rebars is not measured.

Current density was measured for data presented herein is as follows: A section of rebar is embedded in concrete and when the concrete has cured for 30 days. An aluminum plate 2.5 cm×5 cm×1 cm thick was also embedded in the concrete. Current was turned on when it was possible to measure $E_c$ at the Al plate. Sufficient current was applied to keep the pH in the range from about pH 7 to 8. The corrosion potential $E_c$, cathodic polarization potential $E_p$, current I, pH of the concrete, and the resistance $R_c$ of concrete, are measured every day, as was the weight of the rebar. Polarization current was stopped after parameters to be measured reached relatively constant values. The values of potentials $E_p$ and $E_c$ given herein are relative to a HRE.

Rebars are formed from low carbon (less than 1%, preferably less than 0.75%) steel with less than 5%, typically less than 1%, of combined alloying metals. In a dry climate, corrosion of rebars does not take place in an alkaline environment of cement mortar. However when the reinforced concrete structure is in a humid atmosphere which may also contain acidic contaminants such as sulfur dioxide, and/or is wetted with a solution of a salt such as sodium chloride, widely used in Winter to melt ice on the concrete surface, corrosion begins. Once this occurs the alkaline environment is lost because of the generation of acid at the anodic site.

The present invention overcomes the electrolytic corrosion problem by using caluminum-coated rebars, rather than using rods of aluminum of aluminum-rich alloy as a sacrificial anode for uncoated rebars. In operation, the impressed cathodic current is at least sufficient to negate the electrolysis process; preferably the current is high enough to effectively reverse the electrolysis process, current flowing from the anode to the cathode, so that electrons will flow away from the cathodic metal surface to be protected. Of course, current flow and electron flow are in opposite directions; current flows from anode to cathode while electrons flow from cathode to anode.

Figure 1:
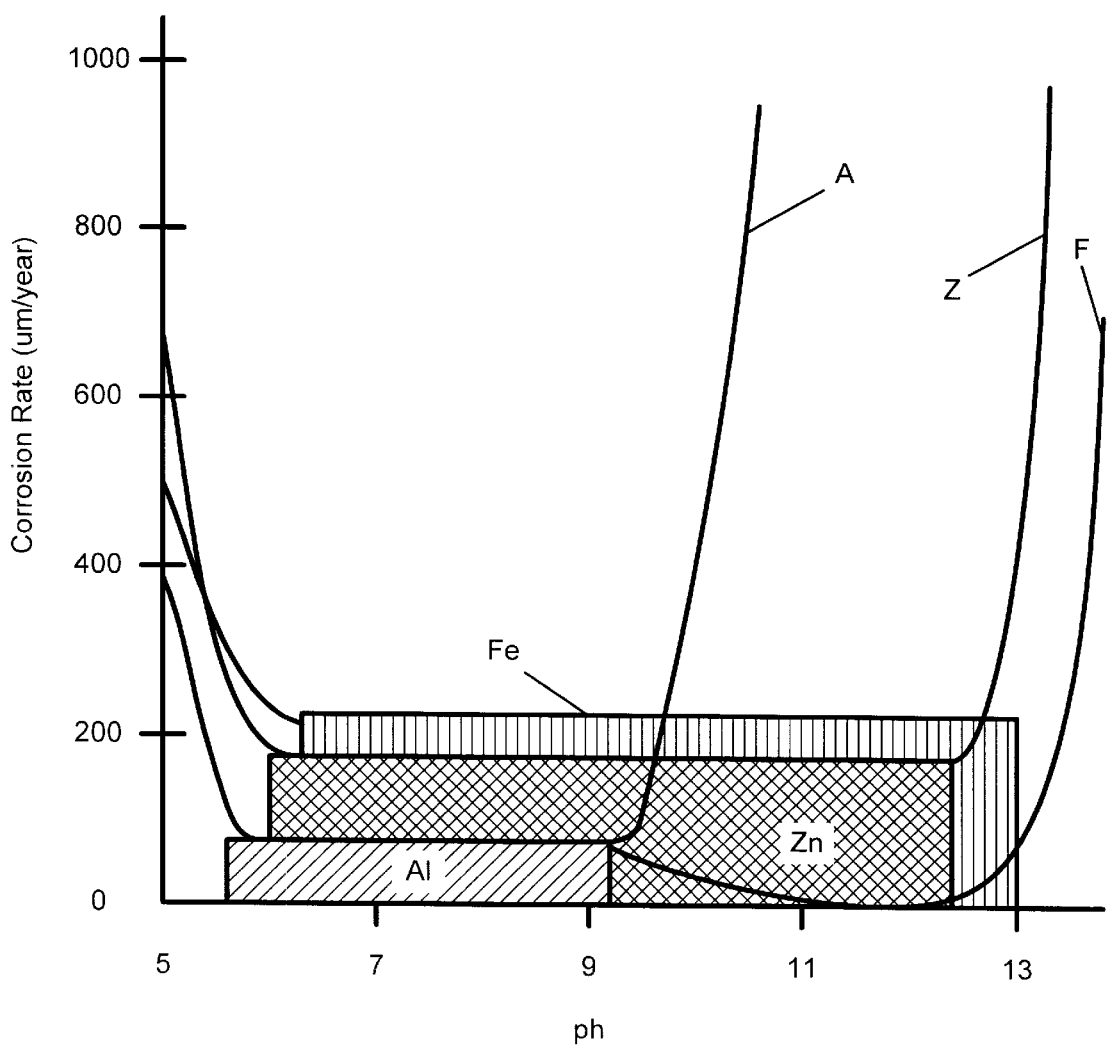
FIG. 1 is a graph showing the relative rates of corrosion of Al, Zn and Fe as a function of pH.

The graph presented in FIG. 1 plots corrosion rate in $\mu$m per year, as a function of pH for rods of Al, Zn and Fe, each rod having the same length of 10 cm and diameter of 2.0 cm. The rods were placed in identical graduated glass cylinders with the same amount of liquid at the same pH in each. Thus 15 cylinders contained aqueous solutions at pH 5, 7, 9, 11 and 13 in groups of three, respectively. Measurements were made over a period of six months using a needle probe pressed into the surface of a rod with the same force, and making measurements of the depth of penetration of the needle with a microscope. The results are plotted to give curve A for the Al rods, curve F for the Fe rods, and curve Z for the Zn rods.

It is evident that Al is corrosion resistant only in the pH range from about 6 to 9; Zn is corrosion resistant in the pH range from about 6 to 12; and Fe is corrosion resistant in the pH range from about 6 to 13.

Figure 4:
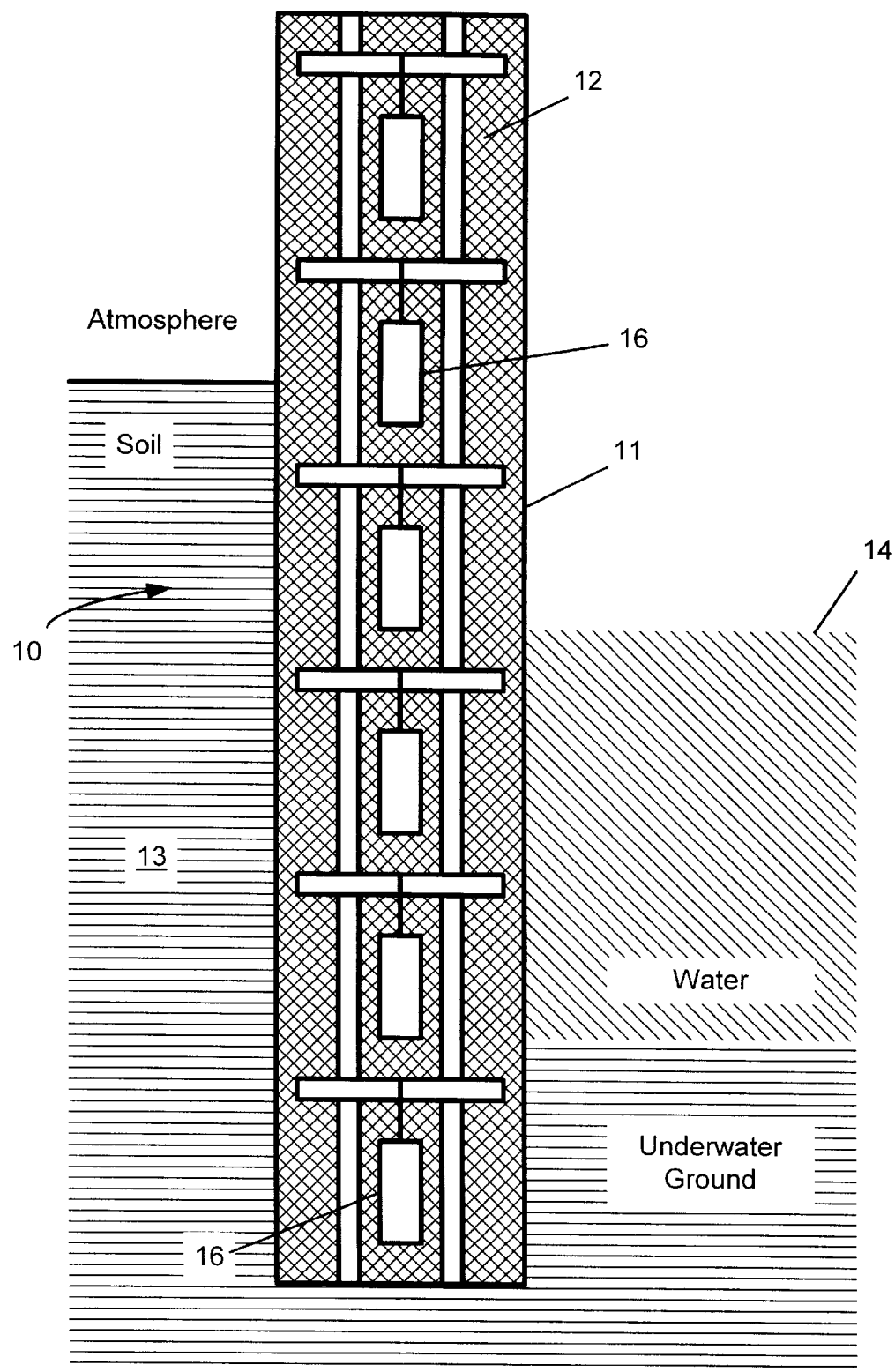
FIG. 4 is a side elevation view schematically illustrating a reinforced concrete structure in which its Al-coated steel rebars are cathodically protected by plural soluble magnesium anodes disposed in spaced apart relationship, all of which are embedded within the structure, and galvanically connected with the cathode.

Referring to FIG. 4 there is illustrated a cathodically protected structure 11 analogous to the one shown in FIG. 2, but in which all anodes are sacrificial anodes (magnesium shown) embedded within the grid of rebars at appropriately spaced apart intervals to obtain the best distribution of cathodic protection. It is evident that this embodiment will only be useful in a newly poured concrete structure, not an existing one.

Figure 5:
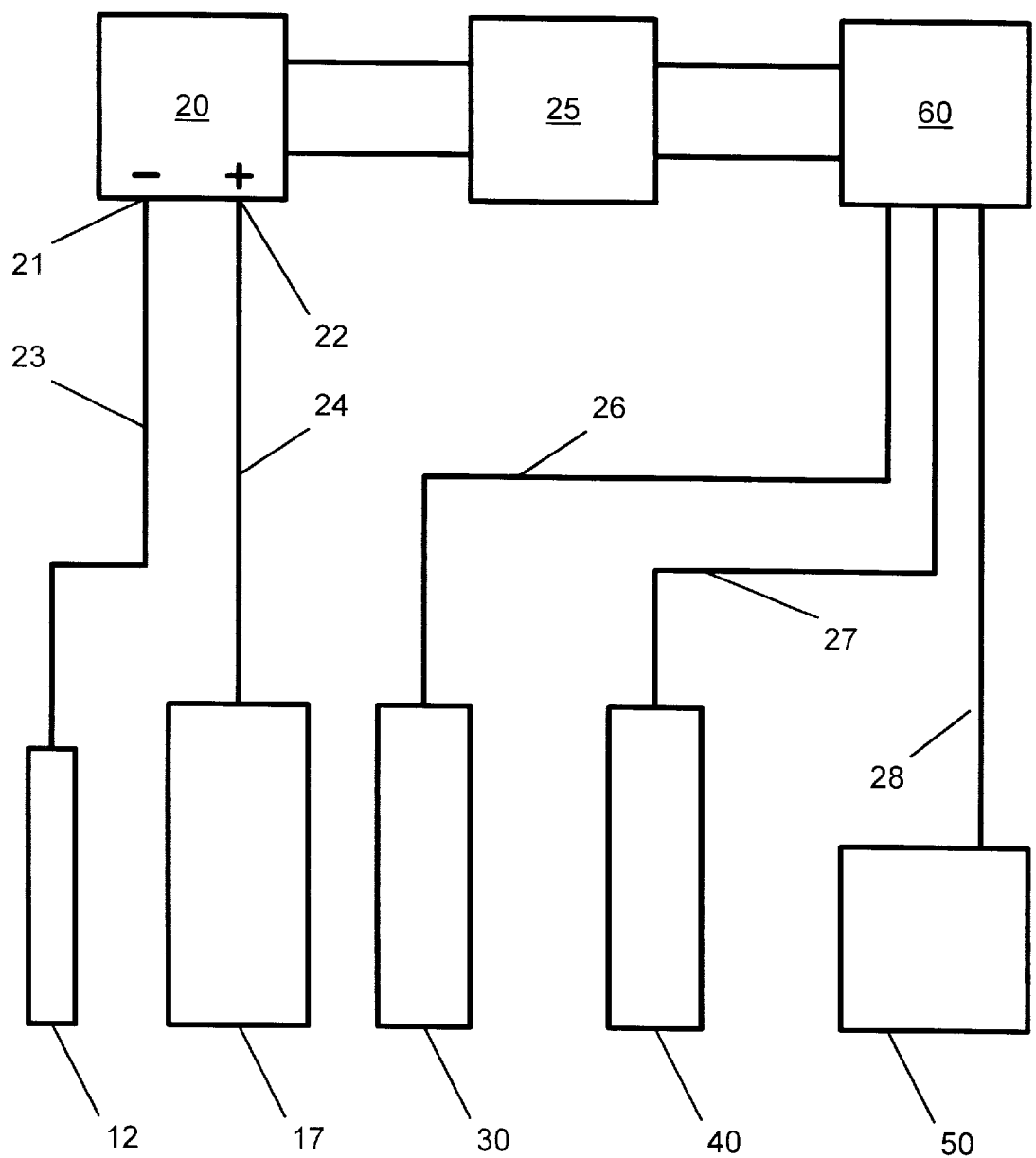
FIG. 5 is a schematic illustration of a system comprising embedded Al-coated rebars cathodically protected by an insoluble anode in an electrical circuit in which current flows to the cathode; a separate circuit monitors the corrosion potential $E_c$ of an essentially pure Al plate or rod; and optionally, a circuit is provided for measuring pH continuously.

Referring further to FIG. 5 there is schematically illustrated a control system in which a grid of Al-coated rebars 12 and anodes 17 are electrically connected to an automatically adjusted direct current power source (electron source) 20 which is directed by a programmable control means 25 to provide a chosen voltage to the rebars 12.

The electron source 20 is a transformer/rectifier or battery having a negative terminal 21 and a positive terminal 22. The terminal 21 is electrically connected to the rebar grid 12 by a lead wire 23; and anodes 17 are connected to terminal 22 with a lead wire 24. Anodes 17 are located at appropriate locations internally and externally relative to the concrete structure so as to provide a desired current density. The location of external anodes, whether inert or soluble, if spaced away from the surface of the concrete structure, depends upon the environment of soil and/or water, but must be proximately disposed relative to the rebars 12, that is, within the concrete structure, or on its surface, or within a short distance from the concrete structure, the distance being a function of the ohmic resistance of the medium between the structure and the anode, so as not to require an impressed current greater than 200 mA/m$^2$. The anodes may be of graphite, or, mixed metal oxide-coated titanium rods known in the art, for example, one sold under the trademark LIDA.

An aluminum corrosion potential sensing member such as plate 30, a reference electrode 40 and a pH electrode 50 are electrically connected to a comparator 60 which measures (i) the corrosion potential of the sensing member relative to a reference electrode until the value stabilizes at a measured stable potential, (ii) the corrosion potential of the Al plate or rod 30, and, preferably also, (iii) the pH of the concrete continuously; and these measurements are transmitted to the comparator 25. The voltage required is in opposition to the external driving voltage because the anodes are permanent. From the circuit voltage and the current, the power required to achieve a desired level of protection is determined. The Al member may be embedded in the reinforced concrete structure, or be embedded in the same concrete used for the structure, but separate from the reinforced structure in a zone outside the reinforced concrete structure.

In this impressed current system it is practical to impose whatever potential is necessary to obtain the current density required by means of the rectifier. Electric current flows in the soil from the buried anodes to the structure to be protected; therefore the anode is connected to the positive pole of the rectifier and the rebar structure is connected to the negative. As before, all lead wires from the rectifier to the anode and to the structure must be electrically insulated. Potential criteria are based on the potential of the structure at the soil interface, at various depths within the soil and on the column at different locations. Conventional means in the comparator 60 are provided to continuously measure the corrosion potential at the surface of the Al plate or rod 30, relative to reference electrode 40, without regard to the corrosion potential at the rebars 12. Programmable control means 25 is then fed actual measurements of potentials at the Al plate or rod and at the reference electrode from the comparator 60, which then provides the appropriate voltage and current density which the electron source 20 delivers to the grid 12, such measurements including potentials sensed at the reference electrode.

It is critical that the corrosion potential of the Al plate or rod 30 be measured, instead of the corrosion potential of the rebars, because it is found that the measurements made at the rebars are not sufficiently reliable. The size of the Al plate or rod is not narrowly critical, but it is placed outside the zone of pH immediately surrounding the rebars. A plate having dimensions of 2.5 cm×5 cm×1 cm thick, or a rod about 10 cm long having a diameter of 2.5 cm is found useful.

To ensure that the cathodic protection is providing a zone of pH in the range from 6 to 9 immediately surrounding each rebar, the pH meter 50 is embedded in the structure, and its sensing probe inserted into the zone immediately surrounding a rebar; preferably several pH meters are embedded in an analogous manner.

The novel system provides for maintenance of the grid 12 essentially free from corrosion in a reinforced concrete structure having a pH in the range from about 6 to 9 measured in a zone immediately surrounding said rebars. The power source 20 provides enough current at a potential $E_p$ which is sufficiently electronegative with respect to the measured corrosion potential $E_c$ at the Al plate, to repress the cathodic potential of the rebars to the cathodic potential of said rebars to within a predetermined range which is correlatable with a pH in the range from about 6 to 9. The power source 20 continuously maintains current at $E_c$ (measured corrosion potential) plus 200 mV (0.2 V) at a current density at which corrosion is minimal, that is, which has been found to provide maximum corrosion protection over an arbitrarily long life of 100 years or more.

Figure 6A:
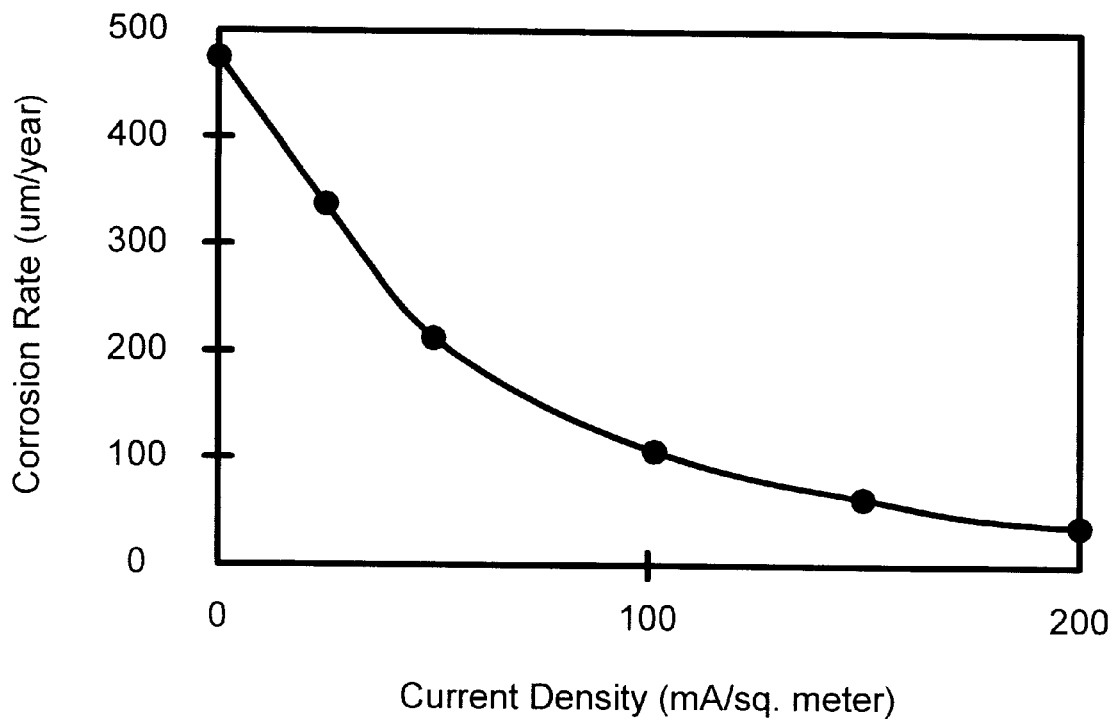
FIG. 6A is a graph of current density as a function of corrosion rate for steel rebars in concrete, using a conventional cathodic protection system, presenting data for current density at which a desired corrosion rate was maintained.

The graph shown in FIG. 6A is a plot of corrosion rate ($\mu$m/yr) of uncoated steel rebars as a function of current density at which the indicated corrosion rate is maintained. It is evident that to obtain a cathodically protected corrosion rate of less than 50 $\mu$m/yr requires a current density of 200 mA/m$^2$.

Figure 6B:
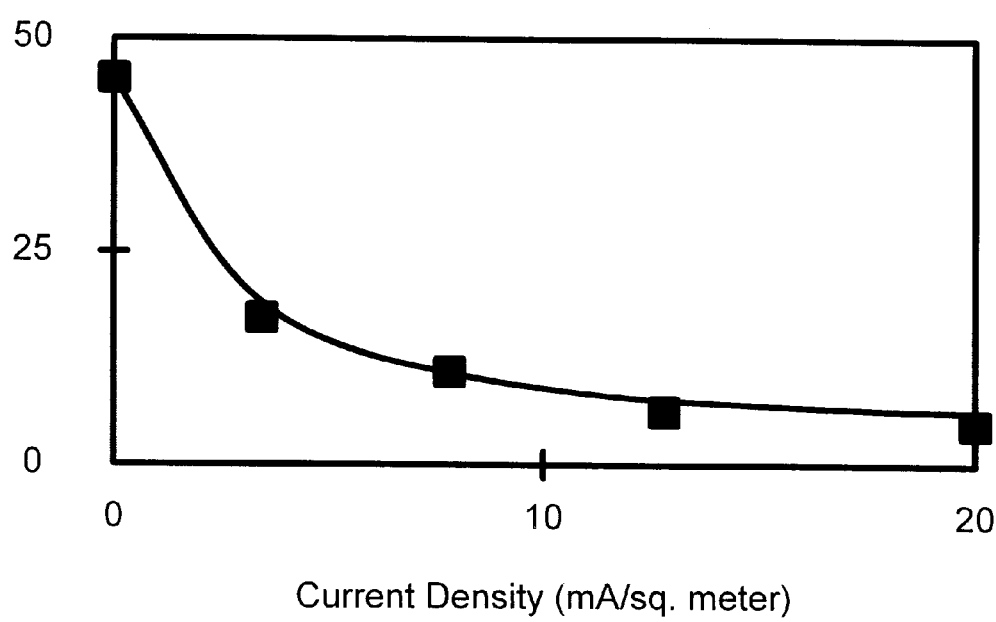
FIG. 6B is a graph of current density as a function of corrosion rate for Al-coated steel rebars in concrete, using the cathodic protection system of this invention, presenting data for current density at which a desired corrosion rate was maintained.
Figure 7:
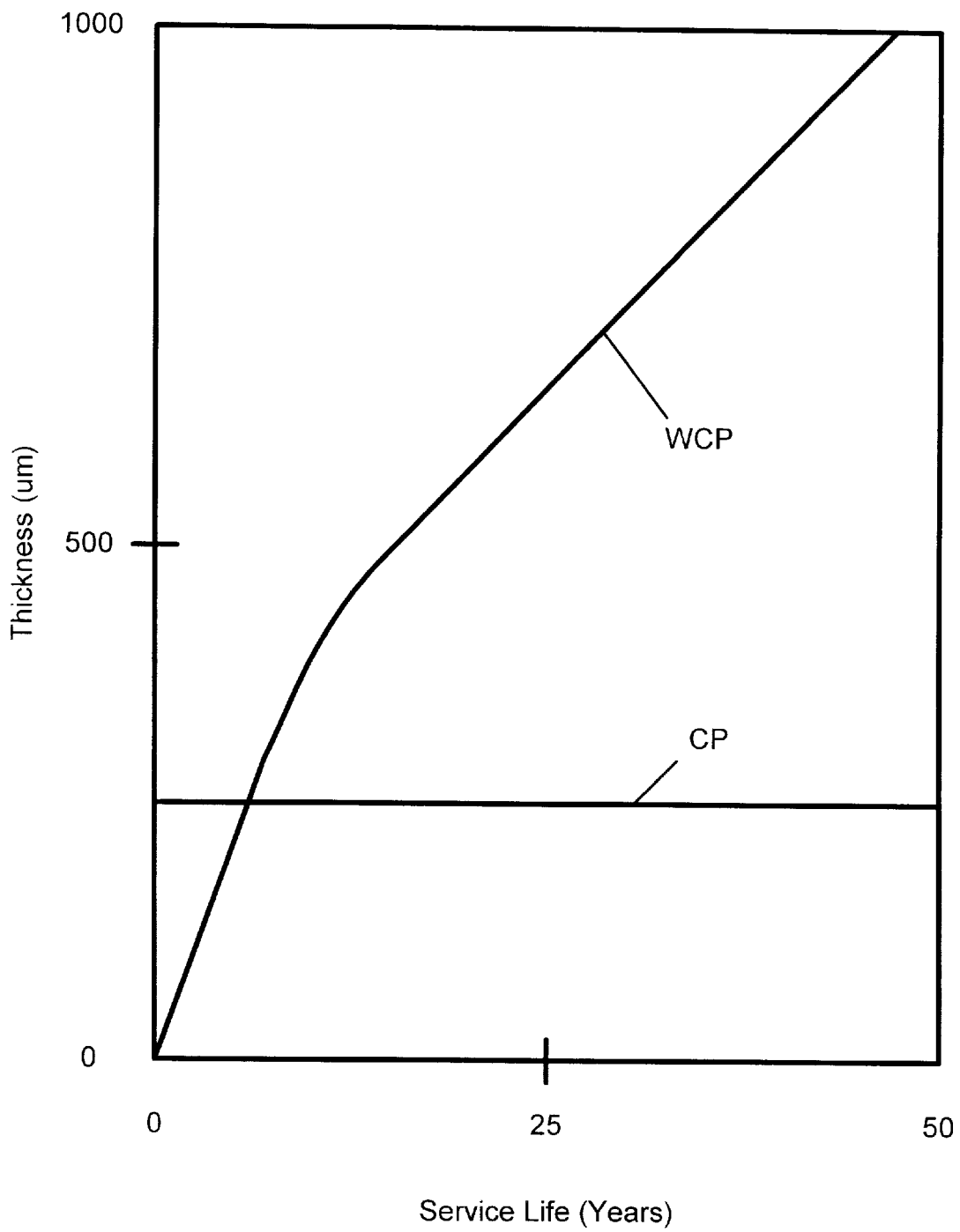
FIG. 7 presents two graphs, one identified as WCP, and the other as CP, the former (WCP) for an Al-coated rebar without impressed current cathodic protection, and the latter (CP) for an Al-coated rebar with impressed current cathodic protection, wherein each provides a chosen length of useful service.

The graph shown in FIG. 6B is a plot of corrosion rate ($\mu$m/yr) of Al-coated steel rebars, coated with a non-porous layer 0.25 mm thick of essentially pure Al, as a function of current density using the system shown in FIG. 5. It is evident that to obtain a corrosion rate of less than 50 $\mu$m/yr requires a current density of about 2 mA/m$^2$, and with current density of 20 mA/m$^2$ the corrosion rate is about 5 $\mu$m/yr.

The following Table 1 presents current requirements for steel rebars, uncoated and Al-coated, at a potential $E_p$=−200 mV to obtain corrosion data in concrete having a pH above 9 to about 13.

TABLE 1

|  | Cathodic Protection Yes or No | Corrosion Rate ($\mu$m/yr) | Current ($\mu$A) |
| --- | --- | --- | --- |
| Uncoated rebars | NO | 60–180 | 0 |
| Uncoated rebars | YES | 20–40 | 420–710 |
| Al-coated rebars | NO | 50–1000 | 0 |
| Al-coated rebars | YEs | <5 | 51–98 |

The foregoing data indicates that if the impressed current is switched on soon after the concrete is poured, excellent protection will be obtained with an Al coating in the thickness indicated above, such protection lasting in excess of 40 years.

The following Table 2 presents current requirements for cathodically protected Al-coated steel rebars at potentials $E_p$=−50, −100 and −200 mV to obtain corrosion data in concrete having a pH above 9 to about 13.

TABLE 2

| Potential (mV) | | Corrosion Rate | Current |
|---|---|---|---|
| -$E_c$ | -$E_p$ | ($\mu$m/yr) | ($\mu$A) |
| 550–600 | 50 | 30–60 | 8–17 |
| 550–600 | 100 | <5 | 19–38 |
| 550–600 | 200 | <5 | 39–77 |

Having thus provided a general discussion, described the overall system and process for cathodically protecting Al-coated rebars in a concrete structure, and illustrated the invention, it will be evident that the invention has provided an effective solution to an old problem. It is therefore to be understood that no undue restrictions are to be imposed by reason of the specific embodiments illustrated and discussed, and particularly that the invention is not restricted to a slavish adherence to the details set forth herein.

I claim:

1. A method of constructing a concrete structure reinforced with steel rebars, comprising, embedding said rebars in concrete having a pH in the range from above 9 to about 13, said rebars having a coating of essentially pure aluminum in the range from about 0.25 mm to 2 mm thick upon which coating is an oxide layer in the range from 0.1 $\mu$m to 100 $\mu$m thick, said oxide layer comprising aluminum oxide and/or hydrated aluminum oxide in a combined aluminum oxide layer which is in direct contact with said concrete;

embedding a corrosion potential sensing member of essentially pure aluminum within said structure;

continuously measuring the corrosion potential at the surface of said corrosion potential sensing member relative to a reference electrode until the value stabilizes at a measured stable potential without measuring the corrosion potential at said rebars;

anodically connecting said source of potential to an anode proximately disposed relative to said rebars;

cathodically connecting said rebars to a source of potential which is sufficiently electronegative with respect to said measured stable potential to repress the cathodic potential of said rebars to within a predetermined range correlatable with a corrosion potential measured at said corrosion potential sensing member; and, continuously maintaining current from said source of electronegative potential at a potential in the range from about 150 mV to less than 300 mV lower than the corrosion potential of said corrosion potential sensing member.

2. The method of claim 1 wherein said rebars are connected to said source of potential to provide an impressed current at a potential in the range from about −900 mV (−0.9 V) to about −1500 mV (−1.5 V) relative to a HRE.

3. The method of claim 2 wherein said coating of essentially pure aluminum and said combined aluminum oxide layer is in the range from greater than 02 mm thick up to about 1 mm thick.

4. A system for the maintenance of a concrete structure reinforced with steel rebars essentially free from corrosion of said rebars, said system comprising, a mass of concrete having a pH in the range from above 9 to about 13 wherein said rebars are electrically interconnected in a grid;

said rebars having a coating of essentially pure aluminum in the range from about 0.25 mm to 2 mm thick upon which coating is an oxide layer in the range from 0.1 $\mu$m to 100 $\mu$m thick, said oxide layer comprising aluminum oxide and hydrated aluminum oxide;

an external power source responsive to a programmable control means to which data is transmitted from a comparator means, connected in serial relationship, said programmable control means being responsive to both said external power source and said comparator means;

measuring means in said comparator means to continuously measure the corrosion potential at the surface of said corrosion potential sensing member relative to a reference electrode until the value stabilizes at a measured stable potential;

means for anodically connecting said external power source of potential to an anode proximately disposed relative to said rebars;

means for cathodically connecting said rebars to said external power source which is sufficiently electronegative with respect to said measured stable potential to repress the cathodic potential of said rebars to within a predetermined range; and, means for continuously maintaining current from said source of electro-negative potential at a potential in the range from about 150 mV to less than 300 mV lower than the corrosion potential of said corrosion potential sensing member.

5. A corrosion protected structure reinforced with steel rebars, said structure comprising, a mass of concrete having a pH in the range from above 9 to about 13 wherein a portion of said mass in a zone within a radius of about 10 mm from the surface of a Al-coated rebar has a pH in the range from 6 to about 9;

said rebars having a coating of essentially pure aluminum in the range from about 0.25 mm to 2 mm thick upon which coating is an oxide layer in the range from 0.1 $\mu$m to 100 $\mu$m thick, said oxide layer comprising aluminum oxide and hydrated aluminum oxide;

a corrosion potential sensing member of essentially pure aluminum embedded within said structure;

means to continuously measure the corrosion potential at the surface of said corrosion potential sensing member relative to a reference electrode until the value stabilizes at a measured stable potential;

means for anodically connecting an external power source of potential to an anode proximately disposed relative to said rebars;

means for cathodically connecting said rebars to said source of potential which is sufficiently electronegative with respect to said measured stable potential to repress the cathodic potential of said rebars to within a predetermined range; and, means for continuously maintaining current from said source of electro-negative potential at a potential in the range from about 150 mV to less than 300 mV lower than the corrosion potential of said corrosion potential sensing member.

6. A corrosion protected structure reinforced with steel rebars, said structure comprising, a mass of concrete having a pH in the range from above 9 to about 13;

said rebars having a coating of essentially pure aluminum in the range from about 0.25 mm to 2 mm thick upon which coating is an oxide layer in the range from 0.1 $\mu$m to 100 $\mu$m thick, said oxide layer comprising aluminum oxide and hydrated aluminum oxide; and, a sacrificial anode in galvanic connection with said rebars and proximately disposed relative thereto.

* * * * *